United States Patent
Wang et al.

(10) Patent No.: US 8,095,199 B2
(45) Date of Patent: Jan. 10, 2012

(54) PORTABLE ELECTROCARDIOGRAPH WITH A NEUTRAL ELECTRODE

(75) Inventors: Weihu Wang, Beijing (CN); Lei Chen, Beijing (CN); Peng Wu, Beijing (CN)

(73) Assignee: Beijing Choice Electronic Technology Co., Ltd., Beijing (CN)

( * ) Notice: Subject to any disclaimer, the term of this patent is extended or adjusted under 35 U.S.C. 154(b) by 561 days.

(21) Appl. No.: 12/159,548

(22) PCT Filed: Apr. 23, 2007

(86) PCT No.: PCT/CN2007/001334
§ 371 (c)(1),
(2), (4) Date: Jun. 27, 2008

(87) PCT Pub. No.: WO2007/121678
PCT Pub. Date: Nov. 1, 2007

(65) Prior Publication Data
US 2009/0137891 A1    May 28, 2009

(30) Foreign Application Priority Data

Apr. 25, 2006 (CN) .......................... 2006 1 0076050

(51) Int. Cl.
*A61B 5/0404* (2006.01)
(52) U.S. Cl. ......... 600/393; 600/372; 600/384; 600/509
(58) Field of Classification Search .................. 600/372, 600/393, 509
See application file for complete search history.

(56) References Cited

U.S. PATENT DOCUMENTS 4,596,256 A * 6/1986 Ascher et al. .................. 600/523
4,869,262 A * 9/1989 Orr et al. ....................... 600/485
(Continued)

FOREIGN PATENT DOCUMENTS
DE                3328599 A1 * 2/1985

OTHER PUBLICATIONS

Bays, Pamela M., Office Communication, Mar. 29, 2011, United States Patent and Trademark Office.

*Primary Examiner* — Lee Cohen
*Assistant Examiner* — Erin M Cardinal
(74) *Attorney, Agent, or Firm* — John C. Serio; Seyfarth Shaw LLP

(57) ABSTRACT

A portable electrocardiograph, characterized in that a clamping cover which tends to close automatically is provided on one end of a housing; a finger hole is provided between the clamping cover and the housing; a lower half of the inner wall of the finger hole is defined on the housing; an upper half of the inner wall of the finger hole is provided on the clamping cover; the lower half of the inner wall is provided with a first electrode; the other end of the housing is provided with a second electrode; and the back face of the housing is provided with a third electrode, in which the first electrode or the third electrode is a neutral electrode. According to the present invention, at least one portion of at least one of the middle finger, the so-called ring finger, and the little finger of the user's hand for grasping the electrocardiograph can contact the neutral electrode, such that the error of the measured result caused by electrical potential fluctuation on the measured person's body can be eliminated.

9 Claims, 5 Drawing Sheets

U.S. PATENT DOCUMENTS

| | | | | |
|---|---|---|---|---|
| D326,521 | S | * | 5/1992 | Sawada ........................ D24/167 |
| 5,511,546 | A | * | 4/1996 | Hon .............................. 600/490 |
| 5,752,920 | A | | 5/1998 | Ogura et al. |
| 6,754,526 | B2 | | 6/2004 | Daynes et al. |
| 7,149,571 | B2 | | 12/2006 | Maeda |
| 7,197,351 | B2 | * | 3/2007 | Umeda et al. .................. 600/393 |
| 2004/0097832 | A1 | | 5/2004 | Adams et al. |
| 2005/0288601 | A1 | * | 12/2005 | Wood et al. .................... 600/513 |
| 2006/0009698 | A1 | * | 1/2006 | Banet et al. .................... 600/485 |

* cited by examiner

PORTABLE ELECTROCARDIOGRAPH WITH A NEUTRAL ELECTRODE

TECHNICAL FIELD

The present invention relates to a portable electrocardiograph with a neutral electrode, which can in real time detect the electrical potential variation on the measured person's body and modify the error of the measured result, such that the electrocardiogram waveform and data can be accurately monitored.

The present invention further relates to a portable electrocardiograph which can simultaneously measure the blood oxygen saturation and the electrocardiogram in high accuracy.

The present invention further relates to a portable electrocardiograph which can independently measure the pulse rate parameter and the blood oxygen saturation parameter, and further judge whether the pulse rate and the respiratory function of measured person are normal.

BACKGROUND OF THE INVENTION

The Chinese patent application No. 200410059061.1 discloses a portable electrocardiograph, whose specification proposes that a neutral electrode can be disposed to eliminate a measurement error which is caused by electrical potential fluctuation of the measured person's body.

However, if the skin of a measured person has an excessively large impedance or has an instable contact with the electrode such that cardiac rate cannot be correctly measured through the electrocardiogram waveform, the pulse rate needs to be measured through a pair of photoelectric cells; or the pulse rate parameter and the blood oxygen saturation parameter are measured independently, further judging whether the pulse rate and the respiratory function of a patient are normal. Unfortunately, it is hard for the measured person to use the portable electrocardiograph and the blood oxygen saturation measuring instrument with his/her two hands simultaneously.

Therefore, the Chinese patent application No. 200410059061.1 cannot simultaneously measure the electrocardiogram and the blood oxygen saturation.

In addition, the neutral electrode provided in the Chinese patent application No. 200410059061.1 is vertical with the longitudinal direction. The shape of the neutral electrode is an elongated rectangular.

Those skilled in the art can easily understand that the case that any finger of any measured person cannot contact the elongated rectangular due to different length of a certain finger of various measured persons and different postures of using the portable electrocardiograph may exist, the so-called neutral electrode may do not work at all.

Conversely, if the neutral electrode is made into a large enough rectangular, the material is wasted and the cost of product is increased, and the shape of the portable electrocardiograph is not beautiful.

SUMMARY OF THE INVENTION

The object of the present invention is to provide a portable electrocardiograph which can in real time detect the electrical potential variation on the measured person's body and modify the error of the measured result, such that the electrocardiogram waveform and data can be more accurately monitored.

Another object of the present invention is to provide a portable electrocardiograph which can simultaneously measure the blood oxygen saturation and the electrocardiogram.

A further object of the present invention is to provide a portable electrocardiograph which can independently measure the pulse rate parameter and the blood oxygen saturation parameter, so as to further judge whether the pulse rate and the respiratory function of the measured person are normal.

Another object of the present invention is to provide a portable electrocardiograph which is with a high measuring accuracy and a high stability.

Therefore, the present invention provides a portable electrocardiograph, characterized in that a clamping cover which automatically tends to close is provided at one end of a housing; a finger hole is defined between the clamping cover and the housing; the lower half of the inner wall of the finger hole is defined on the housing; the upper half of the inner wall of the finger hole is defined on the clamping cover; a first electrode is provided on the lower half of the inner wall; a second electrode is provided at the other end of the housing; a third electrode is provided on the back face of the housing, in which the first electrode or the third electrode is a neutral electrode.

Preferably, the third electrode is in an area of one-quarter cirque, elongated bar, rectangular, oval, circular shape, triangle, L-shape, or reversed L-shape.

Preferably, the second electrode includes two parts, one part of which is the neutral electrode.

Preferably, a photoelectric receiving cell is provided on the inner wall of the lower half of the finger hole, and a light emitting diode is provided at the corresponding position of the inner wall of the upper half of the finger hole.

Preferably, the clamping cover is closed with the housing by means of a torsion spring, and the torsion spring is sleeved on a shaft which is connected with the housing.

Preferably, the clamping cover is closed with the housing by means of a U-shaped spring sheet.

Preferably, the first electrode on the lower half of the inner wall is of a half-ring or semi-oval shape, and the inner wall of the upper half is covered with a half-ring shaped soft material layer.

Preferably, the top face of the photoelectric receiving cell is provided to be at the same surface as the top face of the first electrode, and the top face of the light emitting diode is slightly indented into the surface of the soft material layer.

Preferably, the housing has a data transfer interface with an external storage device.

Preferably, the second electrode is provided to protrude out of the other end of the housing.

According to the portable electrocardiograph of the present invention, the neutral electrode can be of a bending shape, so as to save the material for producing the neutral electrode and make sure that at least one portion of at least one of the middle finger, the so-called ring finger, and the little finger can contact the neutral electrode. Therefore, the error of the measuring result caused by electrical potential fluctuation on the measured person's body is guaranteed to be compensated.

According to the portable electrocardiograph of the present invention, the half-ring or semi-circular shaped electrode in the finger hole is used to contact the finger, thereby increasing contacting area, reducing skin impedance, and improving accuracy of detection in the case that the clamping cover is closed with pressure.

According to the portable electrocardiograph of the present invention, a pair of photoelectric cells can be additionally used. The pair of photoelectric cells can measure the pulse rate when the pulse rate cannot be correctly measured by the electrocardiogram waveform due to excessively large skin impedance or instable contact of another electrode, and it is possible to independently measure the pulse rate parameter and the blood oxygen saturation parameter, so as to further judge whether the pulse rate and the respiratory function of a patient are normal.

BRIEF DESCRIPTION OF THE ACCOMPANYING DRAWINGS

DETAILED DESCRIPTION OF THE PREFERRED EMBODIMENTS

Figure 1:
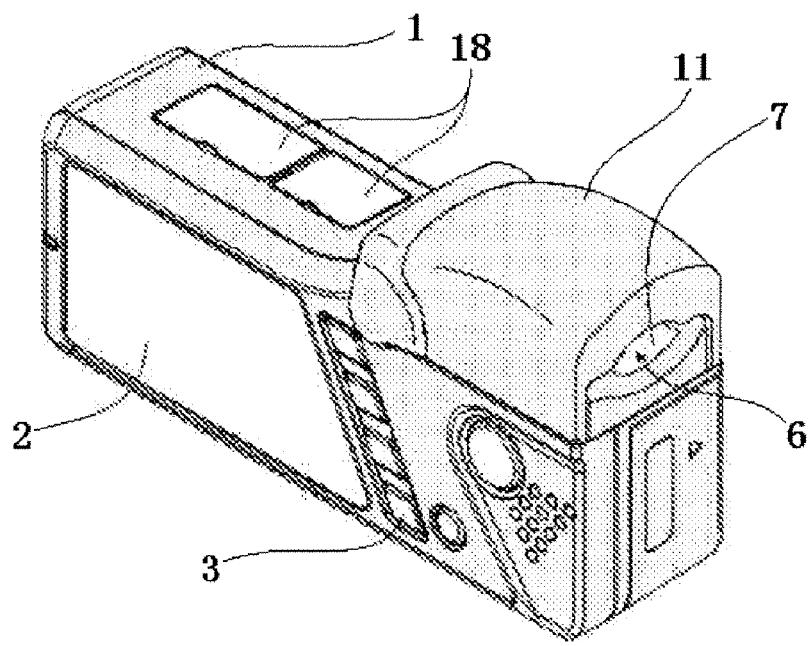
FIG. 1 is a front perspective view of an embodiment of the portable electrocardiograph according to the present invention.

According to an embodiment of the present invention, a front perspective view of a portable electrocardiograph is shown in FIG. 1. The embodiment is related to a pocket-size portable electrocardiograph. A data interface 18 with an external storage device on a housing 1 is located at a position lower than a clamping cover 11, and is disposed in the substantially same level as a first electrode 7, thereby enhancing beautiful looking, saving material, and reducing cost. The shape and position of a display screen 2 and operation buttons 3 in FIG. 1 are schematic, not limiting the present invention.

Figure 2:
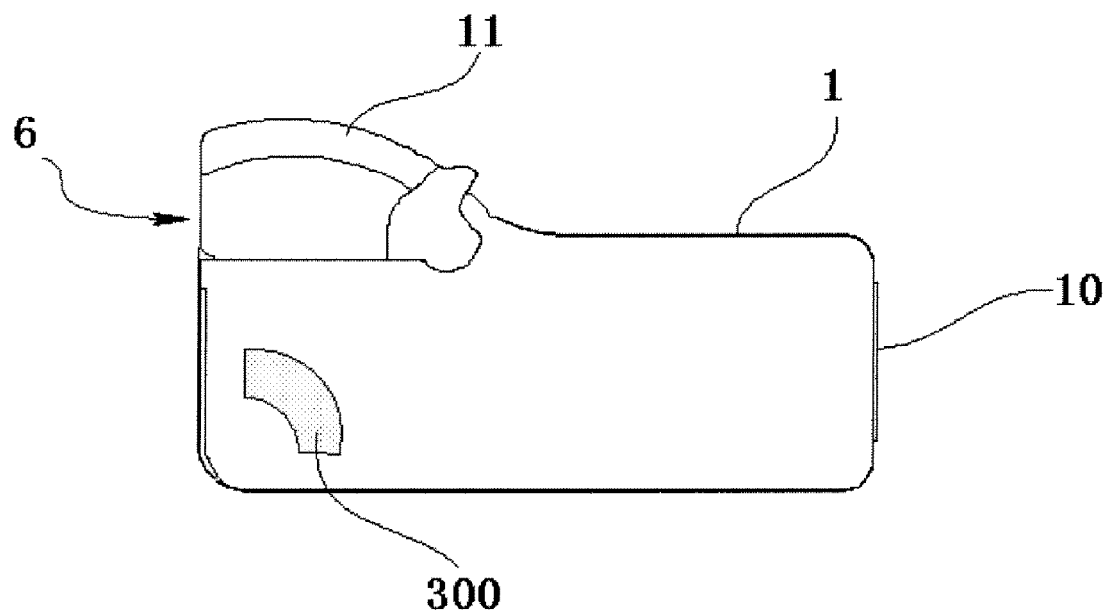
FIG. 2 is a back view of the embodiment of the portable electrocardiograph as shown in FIG. 1.

As iconically seen from FIG. 1, the first electrode 7 is provided on the lower surface of a finger hole 6. As shown in FIG. 2, a neutral electrode 300 is provided on the back face of the portable electrocardiograph, positioned below the first electrode 7 and near the other end of the housing 1 far away from a second electrode 10. The neutral electrode may be of an one-quarter cirque shape and suitable for contacting the side face of the front end of the middle finger.

Figure 3:
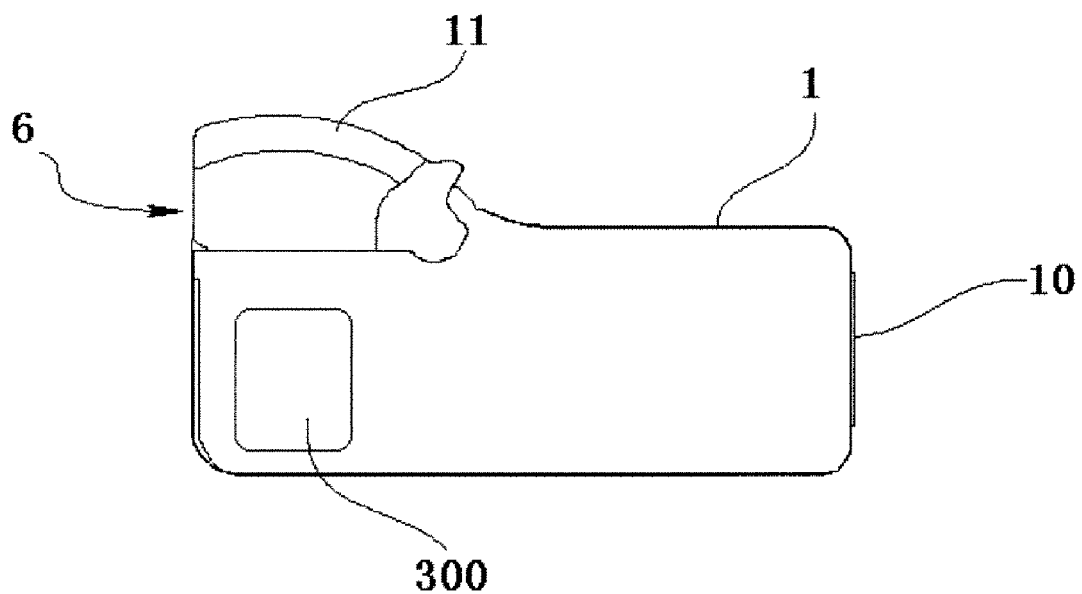
FIG. 3 is a schematic view of another embodiment of the shape and the disposed position of the neutral electrode.
Figure 4:
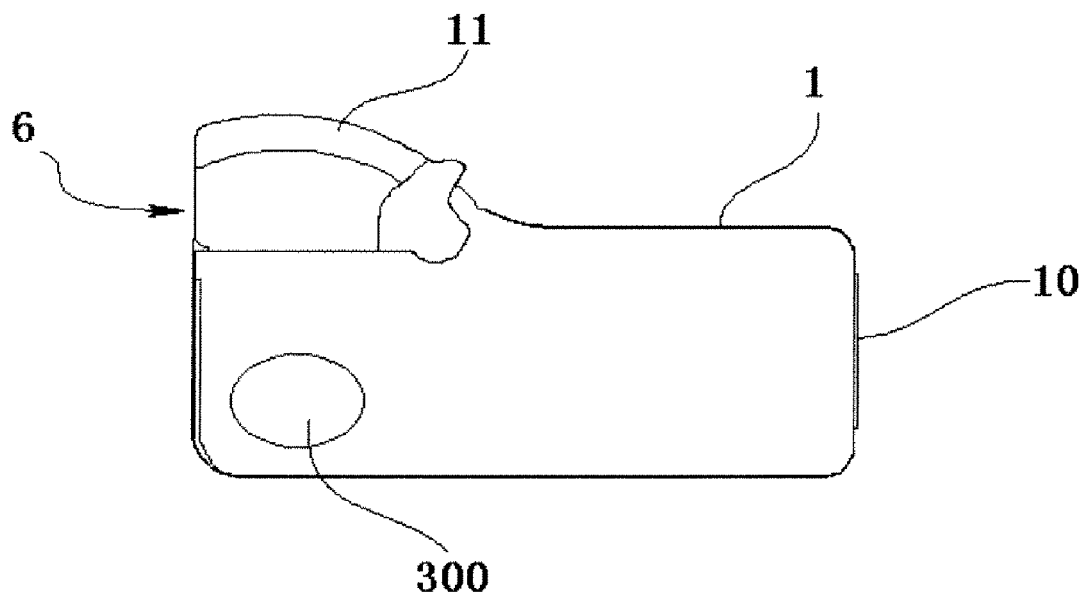
FIG. 4 is a schematic view of another embodiment of the shape and the disposed position of the neutral electrode.
Figure 5:
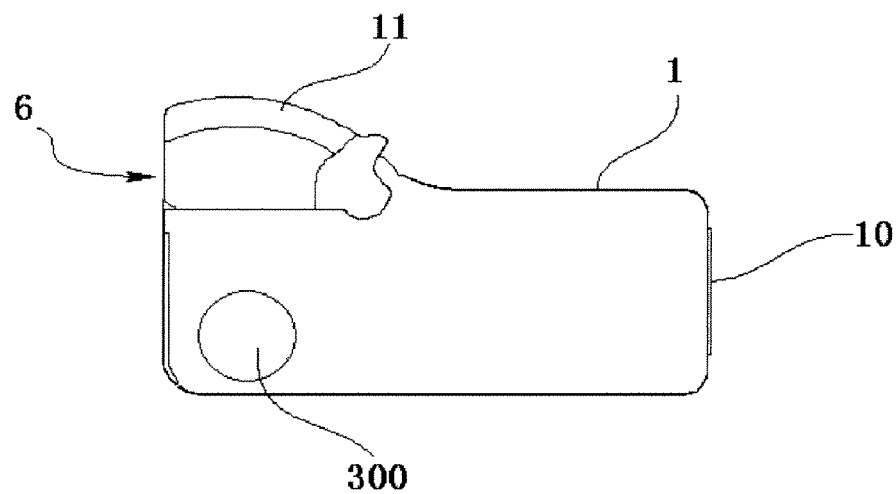
FIG. 5 is a schematic view of another embodiment of the shape and disposed position of the neutral electrode.

Certainly, the neutral electrode 300 may be arranged as an elongated shape or rectangular as shown in FIG. 3, an oval shape as shown in FIG. 4, or a round shape as shown in FIG. 5, etc.

In addition, the electrode 300 may also be provided as a measuring electrode, and the first electrode 7 is changed into the neutral electrode.

Next, another embodiment of the present invention is described in detail in combination with FIG. 6 to FIG. 10.

In the embodiment, as shown in FIG. 6 to FIG. 10, the first electrode 7 is provided at the portion 100 for arranging the first electrode. The second electrode 10 is provided at the portion 200 for arranging the second electrode.

Figure 7:
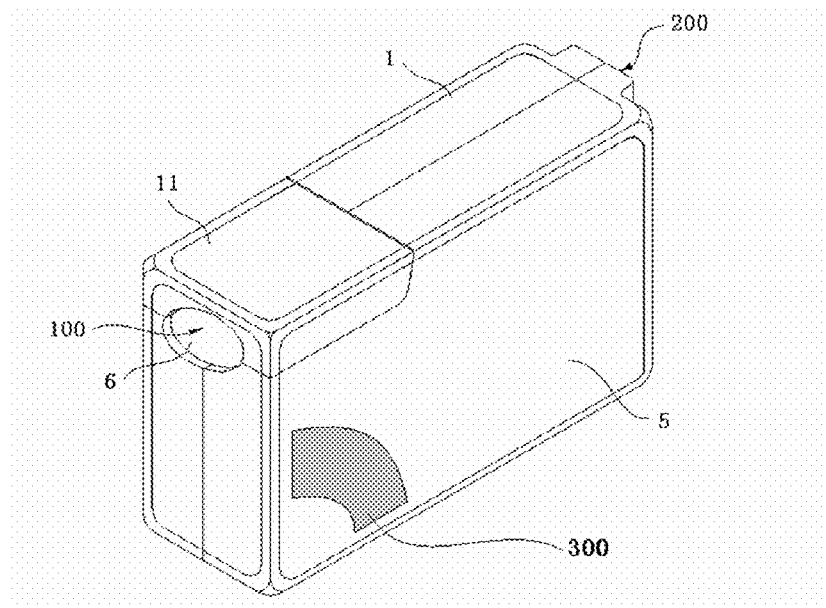
FIG. 7 is a back perspective view of the embodiment of the portable electrocardiograph as shown in FIG. 6.
Figure 10:
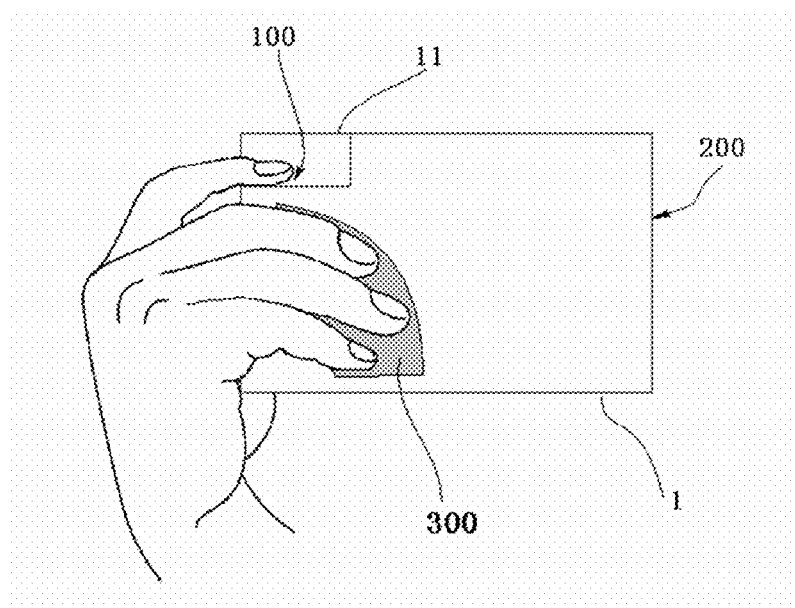
FIG. 10 is a schematic view of a hand-held state of the portable electrocardiograph as shown in FIG. 6.

Specially, as shown in FIG. 7 and FIG. 10, the neutral electrode 300 is provided on the back face of the housing. Particularly, FIG. 10 shows a schematic view of the hand-held state of the electrocardiograph according to the present invention during using, in which the neutral electrode 300 is substantially of an one-quarter cirque shape.

However, the neutral electrode may also be adopted as rectangular, triangle, L-shape, or reversed L-shape, for making sure that at least one portion of at least one finger of the measured person can naturally contact the neutral electrode no matter whether the hand of the measured person is big or small, whether his/her finger is long or short, and what posture the electrocardiograph is held by hand. According to the present invention, the neutral electrode can be made into a bending region, thereby saving material, reducing cost, and further improving aesthetics effect while guaranteeing the reliability.

Next, the other aspects of the embodiment are simply introduced for better understanding of the present invention.

Figure 6:
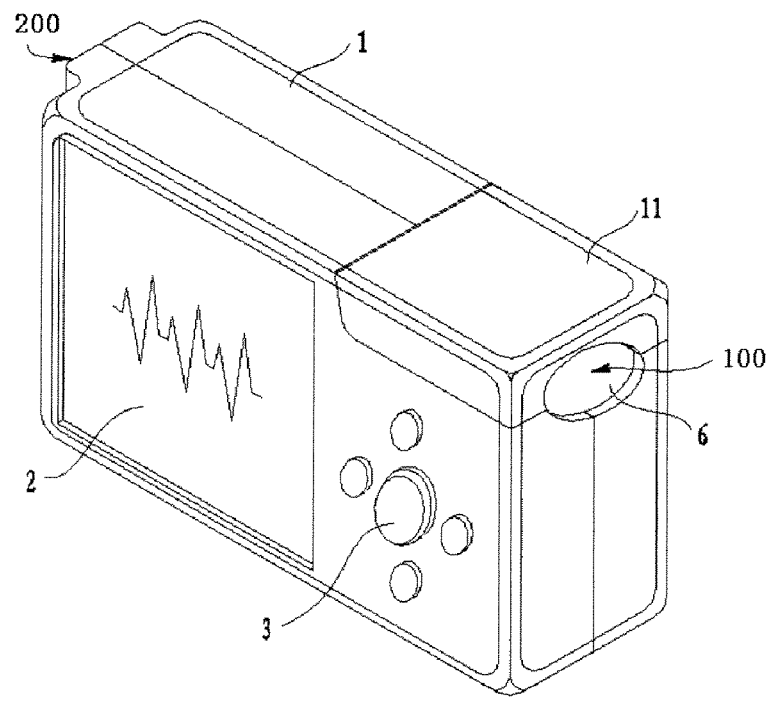
FIG. 6 is a front perspective view of another embodiment of the portable electrocardiograph according to the present invention.
Figure 8:
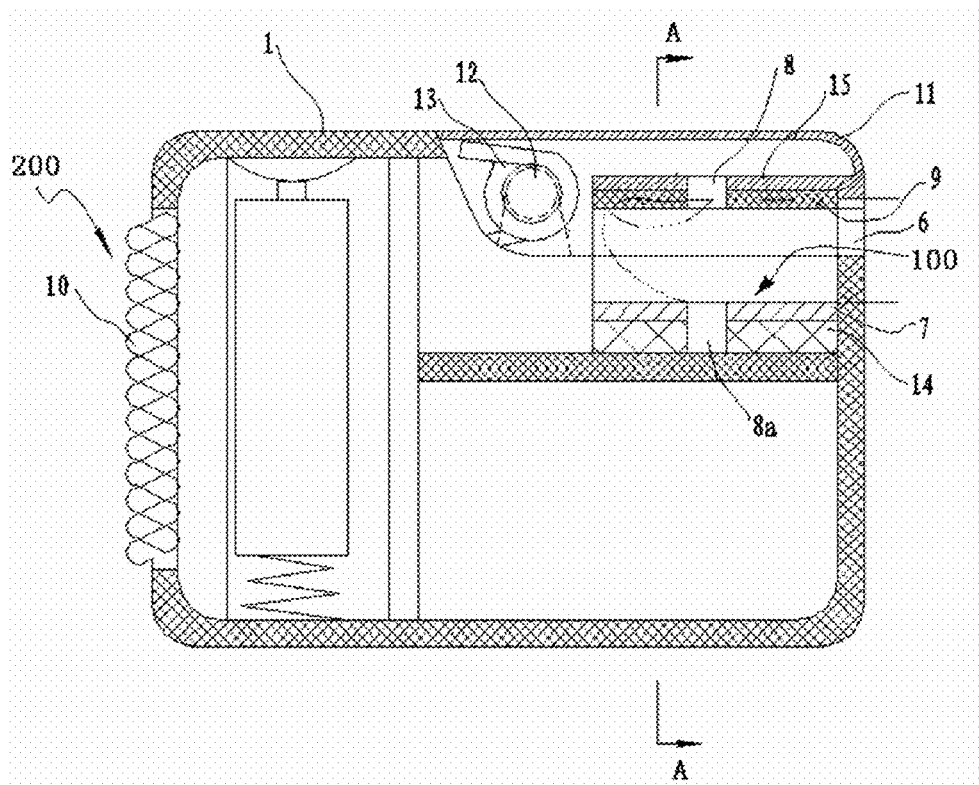
FIG. 8 is a section view of internal structure of the embodiment of the portable electrocardiograph as shown in FIG. 6.

In the embodiment, a housing 1 is of a cuboid shape. A second electrode 10 (as seen in FIG. 8) is provided on the left end face of the housing 1. A keyboard 3 and a display 2 (as seen in FIG. 6) are provided on one front face of the housing 1 for achieving the operation of the instrument and displaying of the electrocardiogram waveform.

A clamping cover 11 is provided on one corner of the right end face of the housing 1 along the longitudinal direction of the housing 1. A shaft 12 is fixed on the housing 1. The clamping cover 11 is fit on the housing 1 by means of a torsion spring 13 provided on the shaft 12, so as to make sure that the clamping cover 11 is automatically closed when no external force is exerted to lift the clamping cover (as seen in FIG. 8). The torsion spring 13 enables the clamping cover 11 tend to rotate around the axis of the shaft 12, so as to make sure that the clamping cover 11 is in the best finger-nipping state.

The installation between the clamping cover 11 and the housing 1 is not in just only one way. Also, a U-shaped spring sheet may be used to realize automatic close of the clamping cover 11.

Figure 9:
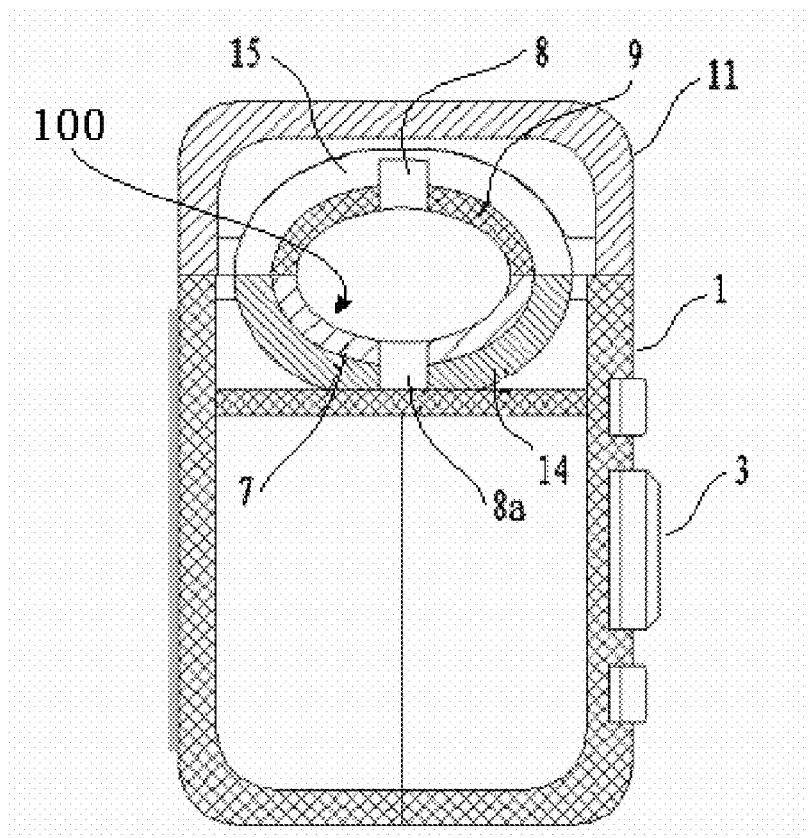
FIG. 9 is a section view of internal structure of the embodiment of the portable electrocardiograph as shown in FIG. 6 along A-A line as shown in FIG. 8.

An oval finger hole 6 (as seen in FIG. 6 to FIG. 9) is formed to open between the clamping cover 11 and the corresponding housing 1. A lower half 14 of the inner wall of the finger hole is defined on the housing 1, and an upper half 15 is defined on the clamping cover 11. The depth of the finger hole 6 is about as long as for inserting the front one to two knuckles of a measuring finger. The inner wall of the hole 6 should be made of insulation material. A first electrode 7 which is made of a half-ring shaped electrical conduction material is provided on the surface of the inner wall of the lower half 14 of the finger hole 6. A semi-oval soft material layer 9 is provided on the inner wall of the upper half 15 of the finger hole 6 (as seen in FIG. 8 and FIG. 9).

To measure the electrocardiogram, the user can follow the following steps, that is, lifting the clamping cover 11 at first, then inserting the forefinger or the middle finger into the finger hole 6 with the finger closely contacting the first electrode 7 due to automatic close of the clamping cover 11 under spring generated pressure, and at the time, putting the second electrode 10 on the left end face closely on the skin of the user's chest.

In the present invention, a pair of photoelectric cells 8 and 8a is provided in the inner walls of the finger hole 6. This pair of photoelectric cells is fit in the inner walls of the finger hole 6 face to face. A light emitting diode 8 is fit on the upper half 15 of the finger hole 6. A photoelectric receiving cell 8a is fit on the lower half 14 of the finger hole 6. The ray emitted from the light emitting diode 8 is generated to pass through the finger inserted into the finger hole 6 and is received by the photoelectric receiving cell 8a in the opposite wall. The top face of the photoelectric receiving cell 8a is provided to be at the same surface as the inner surface of the first electrode 7, so as to avoid damage of this pair of photoelectric cells due to insertion of the measuring finger. The top face of the light emitting diode 8 is slightly indented into the surface of the soft material layer 9. In the embodiment, the light emitting diode 8 is fit on the upper half 15 of the finger hole 6. The photoelectric receiving cell 8a is fit on the lower half 14 of the finger hole 6 (as seen in FIG. 8 and FIG. 9). Actually, this function can still be realized if the photoelectric cells' positions are exchanged.

Particularly, the second electrode 10 can include two parts, one of which is the neutral electrode, such that the error of measurement is further eliminated, and the accuracy of measurement is improved.

The present invention is described above in detail according to a plurality of embodiments. However, those skilled in the art should understand that various modifications and improvements can be made in the present invention, not departing from the spirit of the present invention, and the scope of protection is defined by the attached claims of the present invention.

The invention claimed is:

1. A portable electrocardiograph, comprising:
   a housing having a first end, a second end, and a back face;
   a clamping cover configured to automatically close provided on the first end of the housing (1);
   a finger hole provided between the clamping cover and the housing, the finger hole defined by an inner wall including a lower half defined on the housing and an upper half defined on the clamping cover;
   a first electrode provided on the lower half of the inner wall;
   a second electrode provided on the second end of the housing; and
   a third electrode provided on the back face of the housing, in which the first electrode or the third electrode is a neutral electrode, and the third electrode is configured in a bending shape.

2. The portable electrocardiograph according to claim 1, wherein the third electrode is a one-quarter cirque shape, an oval shape, a circular shape, a triangle shape, an L-shape, or a reversed L-shape.

3. The portable electrocardiograph according to claim 1, further comprising a photoelectric receiving cell provided in the lower half of the inner wall; and a light emitting diode provided at a corresponding position of the upper half of the inner wall.

4. The portable electrocardiograph according to claim 3, wherein a top face of the photoelectric receiving cell is provided to be at the same surface as a top face of the first electrode; and a top face of the light emitting diode is slightly indented into a surface of a soft material layer.

5. The portable electrocardiograph according to claim 1, further comprising a shaft connected with the housing; and a torsion spring configured to automatically close the clamping cover sleeved on the shaft.

6. The portable electrocardiograph according to claim 1, further comprising a U-shaped spring sheet configured to automatically close the clamping cover.

7. The portable electrocardiograph according to claim 1, wherein the first electrode of the lower half of the inner wall is of a semi-oval shape; and a soft material layer of a semi-oval shape is covered on the upper half of the inner wall.

8. The portable electrocardiograph according to claim 1, further comprising a data transfer interface with an external storage device provided on the housing.

9. The portable electrocardiograph according to claim 1, wherein the second electrode is provided to protrude out of the second end of the housing.

* * * * *